United States Patent  
Fisker et al.

(10) Patent No.: US 9,687,324 B2  
(45) Date of Patent: Jun. 27, 2017

(54) SYSTEM AND METHOD FOR DESIGNING POST AND CORE

(75) Inventors: Rune Fisker, Virum (DK); Tais Clausen, Klagshamn (SE); Nikolaj Deichmann, Klagshamn (SE)

(73) Assignee: 3SHAPE A/S, Kobenhavn K (DK)

( * ) Notice: Subject to any disclaimer, the term of this patent is extended or adjusted under 35 U.S.C. 154(b) by 716 days.

(21) Appl. No.: 13/203,316

(22) PCT Filed: Feb. 25, 2010

(86) PCT No.: PCT/DK2010/050048  
§ 371 (c)(1),  
(2), (4) Date: Nov. 4, 2011

(87) PCT Pub. No.: WO2010/097089  
PCT Pub. Date: Sep. 2, 2010

(65) Prior Publication Data  
US 2012/0065943 A1 Mar. 15, 2012

Related U.S. Application Data

(60) Provisional application No. 61/161,850, filed on Mar. 20, 2009.

(30) Foreign Application Priority Data  
Feb. 25, 2009 (DK) ................................ 2009 00264

(51) Int. Cl.  
*G06G 7/48* (2006.01)  
*A61C 13/00* (2006.01)  
(Continued)

(52) U.S. Cl.  
CPC ........ *A61C 13/0004* (2013.01); *A61C 9/0046* (2013.01); *A61C 13/30* (2013.01); *A61C 9/0066* (2013.01)

(58) Field of Classification Search  
CPC ... A61C 13/0004; A61C 9/0046; A61C 13/30; A61C 9/0066  
(Continued)

(56) References Cited

U.S. PATENT DOCUMENTS 4,459,110 A * 7/1984 Jackson ................. A61C 9/002  
433/74  
4,820,159 A * 4/1989 Weissman .............. A61C 13/30  
433/165

(Continued)

FOREIGN PATENT DOCUMENTS

DE 103 39 247 3/2005  
WO WO 2007/062658 6/2007

OTHER PUBLICATIONS

Awad et al., "Fabrication of a Custom-Made Ceramic Post and Core using CAD-CAM Technology" J Prosthet Dent, (2007), vol. 98, pp. 161-162.

(Continued)

*Primary Examiner* — Saif Alhija  
(74) *Attorney, Agent, or Firm* — Buchanan Ingersoll & Rooney PC

(57) ABSTRACT

A system and a computer-implemented method of designing and/or manufacturing a post and core to match a bore of a tooth, said method including the steps of: a) obtaining at least one impression of a set of teeth comprising a bore; b) scanning the impression of the set of teeth comprising the bore; c) providing a three-dimensional scan representation of the impression comprising the bore; d) transforming the three-dimensional scan representation to a three-dimensional positive working model of the set of teeth and the bore; and e) designing a post and core model from the positive working model of the bore. In particular, CAD/CAM design and/or manufacture of post and core.

23 Claims, 13 Drawing Sheets

(51) Int. Cl.
*A61C 13/30* (2006.01)
*A61C 9/00* (2006.01)
(58) Field of Classification Search
USPC .............................................................. 703/7
See application file for complete search history.

(56) References Cited

U.S. PATENT DOCUMENTS

| | | | | |
|---|---|---|---|---|
| 5,437,551 | A * | 8/1995 | Chalifoux | A61C 8/0018 433/172 |
| 5,690,490 | A | 11/1997 | Cannon et al. | |
| 2005/0142517 | A1* | 6/2005 | Frysh | A61C 13/0004 433/173 |
| 2006/0147881 | A1* | 7/2006 | Winter-Moore | A61C 8/005 433/225 |
| 2006/0188844 | A1* | 8/2006 | Dadi | A61C 5/10 433/172 |
| 2008/0050700 | A1 | 2/2008 | Weber et al. | |
| 2009/0220916 | A1 | 9/2009 | Fisker et al. | |

OTHER PUBLICATIONS

Fernandes et al., "Factors Determining Post Selection: A Literature Review" The Journal of Prosthetic Dentistry, (2003), vol. 90, No. 6, pp. 556-562.

Gu et al., "Primary Study of CAD/CAM for Individual Post and Core Restorations" Post Session II, 2nd Meeting of IADR Pan Asian Pacific Federation (PAPF) and the 1st Meeting of IADR Asia/Pacific Region (APR), (2009), 1 Page.

Morgano, "Restoration of Pulpless Teeth: Application of Traditional Principles in Present and Future Contexts" The Journal of Prosthetic Dentistry, (1996), vol. 75, No. 4, pp. 375-380.

Morgano et al., "Foundation Restorations in Fixed Prosthodontics: Current Knowledge and Future Needs" The Journal of Prosthetic Dentistry, (1999), vol. 82, No. 6, pp. 643-657.

Sorensen et al., "Effect of post Adaptation on Fracture Resistance of Endodontically Treated Teeth" The Journal of Prosthetic Dentistry, (1990), vol. 64, No. 4, pp. 419-424.

Srinivasan, "Unconventional Prosthodontics: Post, Core, and Crown Technique" Journal of Indian Prosthodontic Society, (2007), vol. 7, No. 4, pp. 191-195.

Streaker et al., "The Milled Ceramic Post and Core: A Functional and Esthetic Alternative" The Journal of Prosthetic Dentistry, (2007), vol. 98, No. 6, pp. 486-487.

International Search Report (Form PCT/ISA/210) and the Written Opinion of the International Searching Authority (Form PCT/ISA/237) dated Aug. 8, 2010. issued in the corresponding International Application No. PCT/DK2010/050048.

Notification of Transmittal of the International Preliminary Report on Patentability (Forms PCT/IPEA/416 and PCT/separate Sheet/409) dated May 4, 2011, issued in the corresponding international Application No. PCT/DK2010/050048.

* cited by examiner

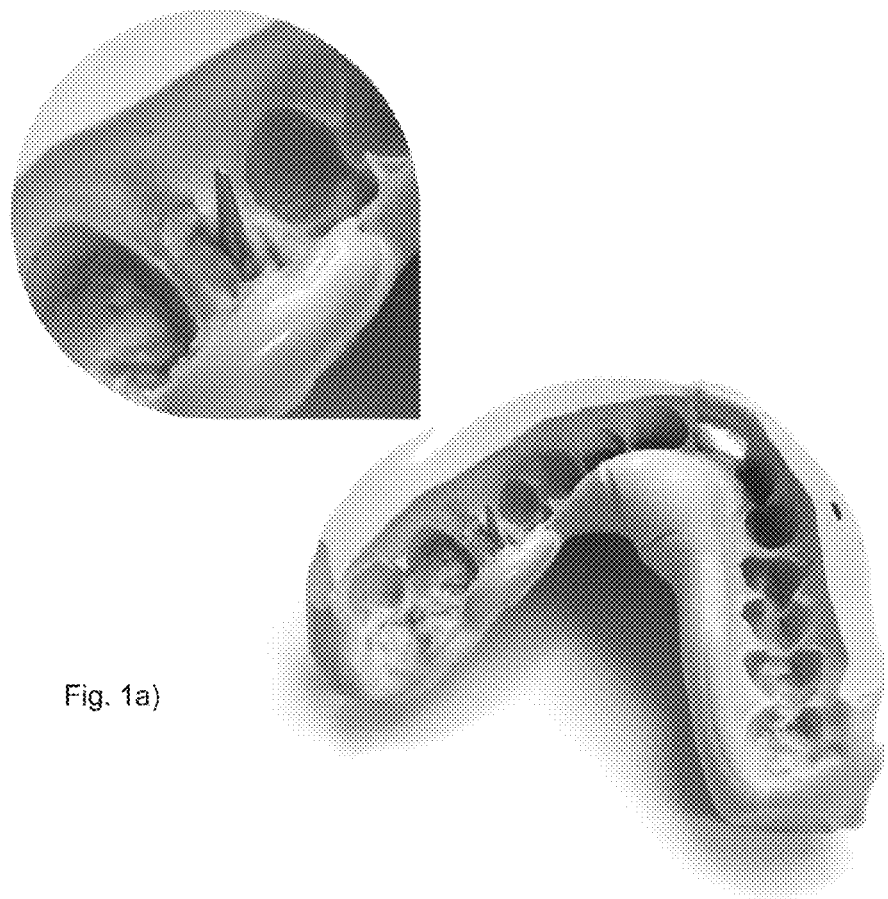
Fig. 1a)
Fig. 1b)
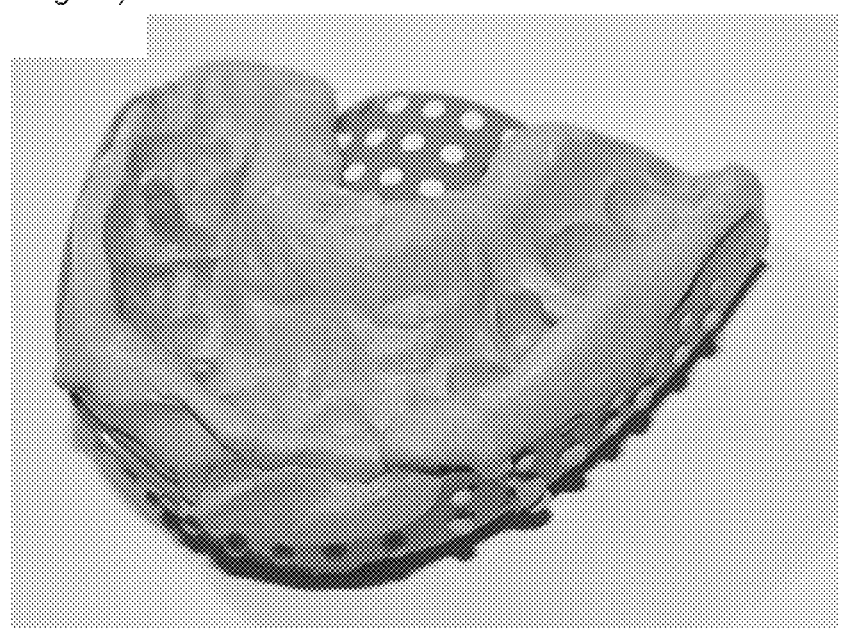

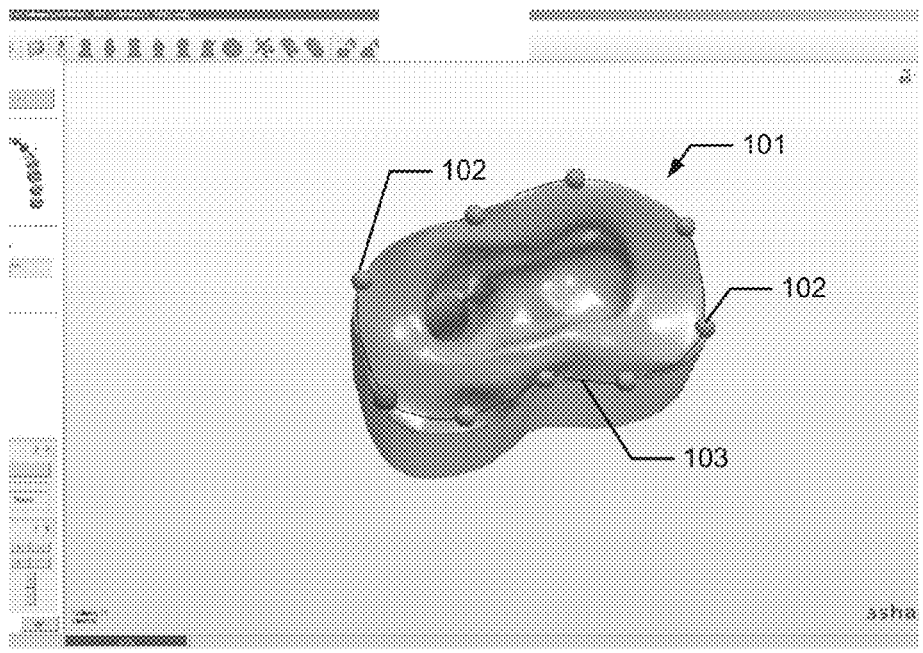
Fig.10a)
Fig.10b)
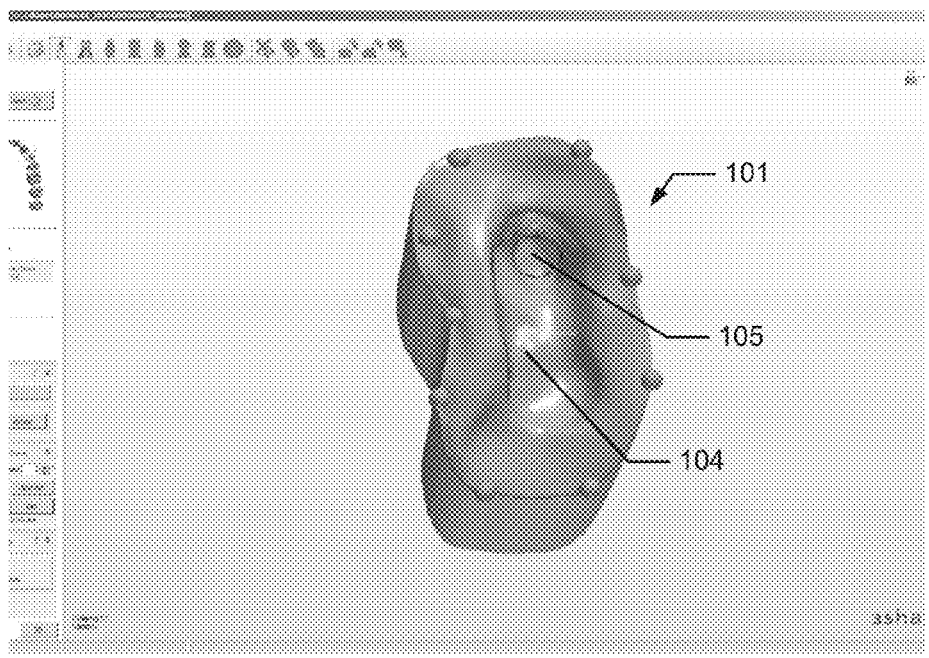

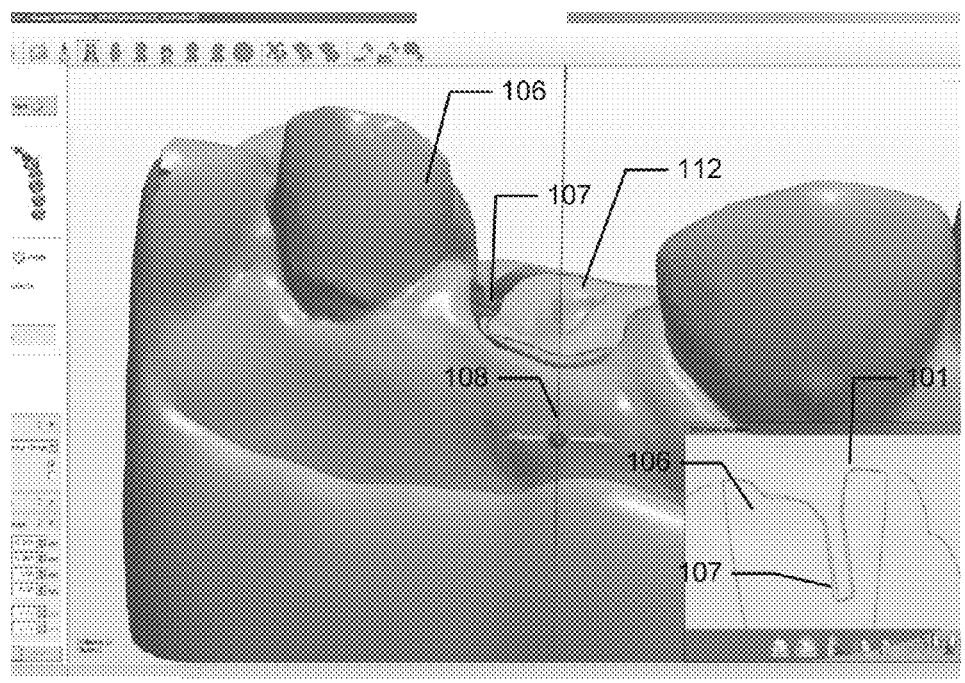
Fig.10e)
Fig.10f)
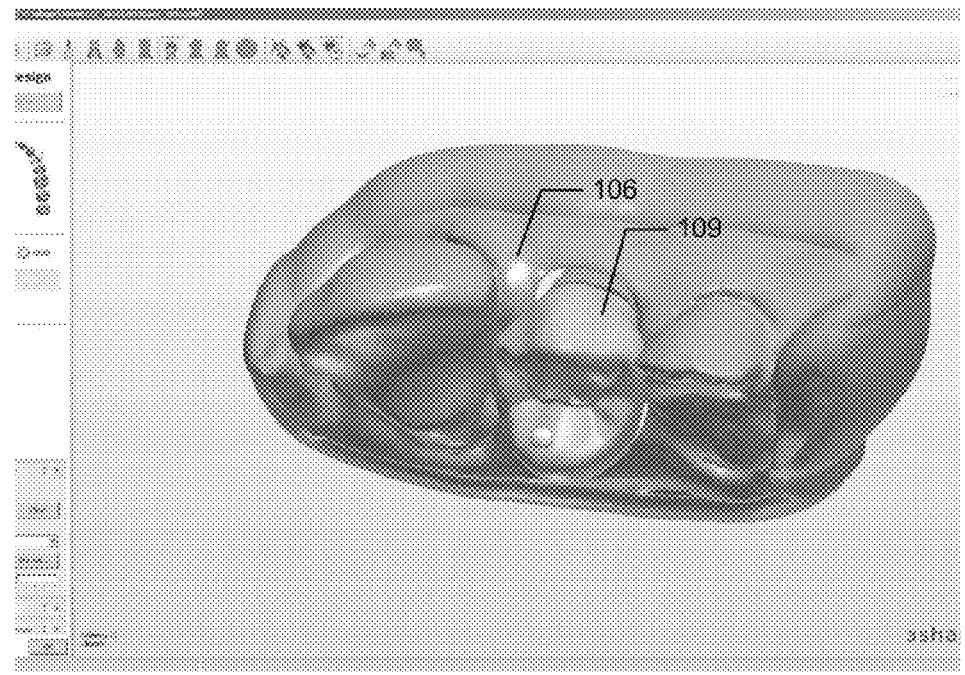

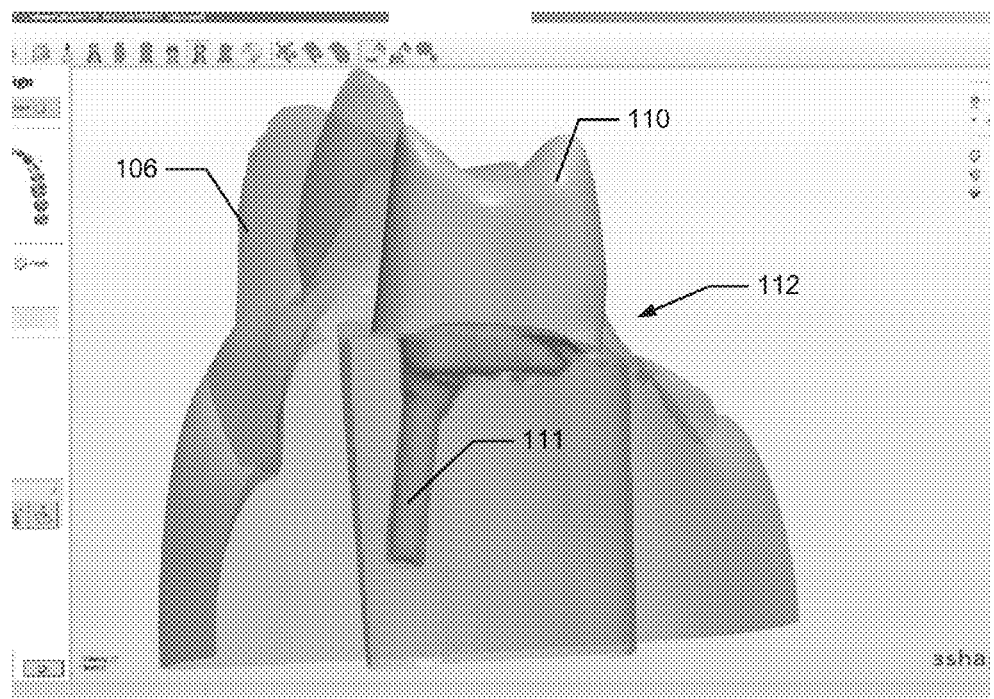
Fig.10i
Fig.11
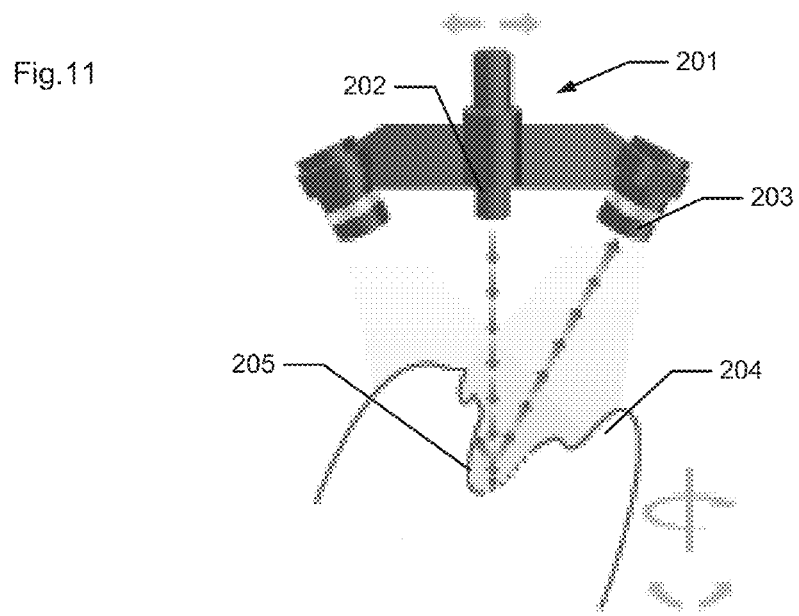

SYSTEM AND METHOD FOR DESIGNING POST AND CORE

FIELD OF INVENTION

The present invention relates to a system and a method for providing the design of a dental post and core, in particular relating to CAD/CAM design/manufacture of post and core. A post and core is typically a part of a dental restoration. Moreover, the invention relates to a computer-readable medium for implementing such a system on a computer.

BACKGROUND OF INVENTION

A post and core is a dental restoration used to sufficiently build-up tooth structure for future restoration with a crown when there is not enough tooth structure to properly retain the crown due to loss of tooth structure to either decay or fracture. In many cases the dental root is removed leaving an empty root canal in the tooth. Typically a thin rigid post (e.g. metal post) is inserted into the root canal and this post provides retention for a "core" which is a build up of material that replaces the lost tooth structure. The post can be cemented within the root canal and the core, which is an artificial preparation provides retention for the crown or coping replacing the tooth. The term "post and core" is also referred to as "post-and-core" and "inlay core". Post and core restorations are often characterised as "foundation restorations".

In a root canal procedure the nerve of the tooth is typically removed by the dentist using a dental drill, a so called endodontic procedure, leaving a bore in the tooth. In many cases a special post can be provided that matches the shape of the drill and after drilling the post can be directly cemented in the bore. However, the tooth root canal may have a non-regular structure and the bore in the tooth after removing the root is often also irregular, but even for the regular shapes the depth of the bore may be unknown. No post can thereby match the bore and a custom post must be provided.

A typical procedure when designing a post and core is that the dentist provides an impression of the prepared tooth with the bore and possibly also adjacent teeth and sends it typically to a dental technician at a dental laboratory. From this impression a dental model, such as a gypsum model, can be poured, and the dental restoration including the post and core can now be build from the dental model. The dental technician typically builds the post and core in wax, and then performs an investment casting, such that the real post and core is manufactured in a suitable material, e.g. a metal alloy.

The article "Fabrication of a custom-made ceramic post and core using CAD-CAM technology" by Awad et al. from J. Prosthet Dent 2007; 98; 161-162 discloses the use of CAD-CAM technology to fabricate a custom-made ceramic post and core, which includes the fabrication of a direct acrylic resin pattern, i.e. wax, to capture the anatomy of the canal, and then the pattern is scanned, milled and sintered. The pattern is fabricated by the manual method of lubricating the canal with either water or saliva, then placing autopolymerizing acrylic resin on the plastic core with a brush and placing the post into the canal. The post is maintained in position for a few seconds, and then quickly removed for determining if the entire anatomy of the canal was recorded. If needed, more acrylic resin is applied to the post, the post is placed back into canal before it completely polymerizes, and then moving the post in and out of the canal until it is passively inserted and removed. Then the post pattern is placed into the canal and the core is added. The post and core pattern is attached to the scanning ring of the CAD system, and then scanning and milling of the patterns is performed. Thus according to the disclosure the scanner of the CAD system is used to scan the shape of a custom-made plastic sample post and core for manufacturing the real ceramic post and core on a milling machine, so called copy milling.

The article "Primary Study of CAD/CAM for Individual Post and Core Restorations" by Gu et al. from 2nd Meeting of IADR Pan Asian Pacific Federation and the 1st Meeting of IADR Asia/Pacific Region, September 2009, discloses that a pair of post and core plaster casts with preparations of different positions and shapes were fabricated. The plaster casts were then scanned by CGI (Capture Geometrical Inside) method to acquire the 3-dimensional data. The 3-dimenisional designs of post and core restorations were then conducted in CAD/CAM software for prosthodontics, and at last the restorations were machined by means of rapid prototyping to convert the 3-dimensional data of CAD to objects of resin. Thus according to the disclosure post and core plaster casts are scanned before designing and manufacturing the real resin post and core.

Thus it remains a problem to provide a more efficient and high quality CAD-CAM procedure for providing post and cores.

SUMMARY OF THE INVENTION

Disclosed is a computer-implemented method of designing and/or manufacturing a post and core to match a bore of a tooth, said method comprising the steps of:
a) obtaining at least one impression of a set of teeth comprising a bore;
b) scanning the impression of the set of teeth comprising the bore;
c) providing a three-dimensional scan representation of the impression comprising the bore;
d) transforming the three-dimensional scan representation to a three-dimensional positive working model of the set of teeth and the bore; and
e) designing a post and core model from the positive working model of the bore.

Thus it is an advantage that the method provides a way of resolving the structure of a tooth bore to provide a matching post and core. Thus the method solves the problem that during conventional 3D scanning of a dental gypsum model with a bore it is virtually impossible for the scanner to resolve the structure of the narrow tooth cavity, i.e. the bore, as seen in FIG. 11. Thus traditionally it is not possible to examine the structure or shape of the bore in the prepared tooth. This is because 3D scanners for scanning, e.g. dental models, uses the well-known triangulation principle to obtain the 3D scan, and if the bore is too narrow or has a non-regular shape, the sensors of the scanner, e.g. camera or light projector, cannot measure all points in the bore.

Impression scanning is known in the art. However, this invention relates to scanning of the impression of a bore. A tooth impression will provide a negative representation of the tooth, i.e. the tooth will be a hole in the impression, however an impression of a bore/cavity will be a spike in the impression. Thus when scanning an impression of a bore, a good result of the scanning can be obtained, because there will no areas of the bore that the scanner cannot gain access to, because the bore in the impression is formed like a spike and not like a narrow cavity as in a positive model. Thus an impression of the bore becomes the basis of the post and core model, in particular in designing a post matching the bore.

However, in order to get a good representation of the unmodified teeth, the impression scan can be inverted or transformed to a positive model, where the teeth have an extent or expand instead of being holes. In this virtual positive model, the bore is a narrow cavity.

The virtual 3D model which is transformed or inverted from the impression scan representation may be denoted a virtual working model, because the post and core can be formed using the virtual working model. The virtual working model may be modified, adjusted, formed and shaped such that it resembles a physical model, e.g. resembling a gypsum model, so that the visual appearance of the virtual working model makes it easy for a dental technician to perform the designing, if he/she is used to working with a physical model.

The post and core can be designed using the virtual working model, such that it is easy for the dental technician to visualize how the real post and core will look and fit into the mouth of a patient.

Transforming or inverting the scan representation of the impression to the positive working model can be performed by rotating the representation, inverting the points of the representation, and/or performed in other ways known to the skilled person etc.

The positive working model may be created by e.g. deleting some of the sides, if they for instance provide shade or shadow for some of the teeth in the model, a base may be created for the positive virtual working model, and the post and core in the virtual working model may be marked and provided as a section which can be virtually removed or taken out from the model.

Traditionally, due to problems of generating a correct virtual 3D model from scanning a teeth impression, impression scanning is often only a supplement to the gypsum dental model. However, when designing a post and core according to the present invention, casting the dental model in e.g. gypsum may be omitted thereby providing a more efficient and high quality CAD/CAM procedure and reducing the risk of error.

It is an advantage that CAD/CAM technology for designing and manufacturing dental restorations result in improved quality, reduced cost and facilitation of the possibility to manufacture in attractive materials otherwise not available, e.g. zircon.

It is an advantage that CAD/CAM technology provides high accuracy, since accuracy requirements for dental restorations are very high otherwise the dental restoration will not be visual appealing, fit onto the teeth, could cause pain or cause infections.

Thus CAD/CAM technology can be used for designing and manufacturing dental restorations. The first step in a conventional or traditional CAD manufacturing process is to create a 3-dimensional dental model of the patient's teeth. This can conventionally be provided by 3D scanning a dental gypsum model. The 3-dimensional replicas of the teeth are imported into a CAD program, where the entire dental restoration or a substructure is designed. The final restoration 3D design is then manufactured e.g. using a milling machine, 3D printer, rapid prototyping manufacturing or other manufacturing equipment.

It is thus an advantage of the present method that the dental gypsum model might not need to be manufactured, because the post and core can be designed completely digitally without using any manually prepared physical model. The dental technician needs therefore not to pour the gypsum model, and this saves time and material, so the turn-around time is reduced, which is an advantage.

Some dental technicians may however still wish to have a physical working model, on which they can test and adjust a post and core model. It is therefore an advantage that the post and core model can be manufactured according to the present method, and simultaneously a physical working model can be manufactured also using CAD/CAM. Thus the turn-around time is still reduced, because the post and core model and the physical working model can be manufactured simultaneously, and the designing or manufacturing of one of them is not dependent on the designing and manufacture of the other one.

Manufacturing according to the present method may be performed using CAM technologies, such as:
  milling;
  3D printing;
  3D laser sintering;
  moulding.

Materials to be used in the manufacturing may be:
  zircon oxide;
  ceramics;
  wax;
  precious alloys;
  non-precious alloys.

According to an aspect of the invention a method for designing and/or manufacturing a post and core to match a bore of a tooth is disclosed, said method comprising the steps of:
  scanning at least one impression of the bore, preferably a jaw dental impression comprising an impression of the bore; thereby
  obtaining a three dimensional model of the impression, said three dimensional model comprising a positive model of the bore, and
  creating a post and core model from the positive model of the bore.

In an embodiment the step of obtaining a three-dimensional model of the impression comprises providing a three-dimensional scan representation of the impression, and transforming the three-dimensional scan representation of the impression to the virtual three-dimensional model comprising the bore.

In some embodiments the virtual three-dimensional working model is configured to be trimmed, and/or provided with a base, and/or articulation tested, and/or provided with sectioned preparations preserving the gingival.

In some embodiments manufacturing comprises manufacturing the post and core design and/or manufacturing the working model.

In some embodiments the step of scanning at least one impression comprises:
  f) performing an initial scan of the impression;
  g) creating a visibility function based on a virtual model of the scanner performing the scanning and the initial scan of the impression, said visibility function being capable of evaluating the coverage of areas of interest of the impression by at least one predetermined scan sequence;
  h) establishing at least one scan sequence based on the evaluation of the visibility function;
  i) performing a scan of the impression using said at least one scan sequence;
  j) optionally repeating steps h) and i) at least once until the three dimensional model of the impression is obtained.

The above embodiment may be called adaptive scanning, because the scanning is adapted to the specific object, or in this case, impression. Adaptive scanning is an advantage because it enables that full geometrical coverage of the impression is obtained. A problem with 3D scanning, using e.g. structured light, is that both the camera and light pattern of the scanner need to "see" each surface point at the same time to be able to make a 3D reconstruction of that particular point. If this is not fulfilled, this leads to "occluded" or uncovered areas which appear as surface holes in the final scan, i.e. areas without surface measurement information. Holes in the scan are in most cases undesirable or unacceptable both from a visual and application point of view. However, when using adaptive scanning the initially uncovered areas will also be covered, because the scanner software registers where the uncovered areas are on the impression and then performs scanning sequences directed to these specific areas.

In a further object of the invention a model for the post may be provided independently and/or separately and/or in a separate step from creating a model of the core. I.e. the post must match the bore and the core must match the post and the adjacent teeth, and vice versa: the post must match the core matching the adjacent teeth. Creating models of post and core in separate steps further requires a step of merging/combining the models.

The term "post and core" comprises the post being inserted in the bore and the core attached to the post becoming retention for a dental restoration. The post and core can be designed and/or cast and/or designed and/or manufactured in one piece or in two or more pieces. Thus, the "post and core model" is a 3D model of a "post and core".

The term "post" refers to the part of a post and core being inserted in the bore. Thus, a "post model" is a 3D model of the post only.

The term "core" refers to the part of a post and core that is retention of a dental restoration. Thus, a "core model" is a 3D model of the core only.

The term "bore" refers to a drilled cavity/bore in a prepared tooth. A "bore model" is a 3D model of the bore.

The term dental impression may also be denoted jaw impression.

When removing the tooth root/tooth nerve the dentist have used one or more dental drills. Thus, the shape of the resulting tooth bore is at least partly determined by the shape and/or type of the drill(s) processing the bore. In a further embodiment of the invention the post and core model and/or the post model is matched with the shape of the dental drill that created the bore. This is provided to improve the post and core model. Matching the shape can be merging and/or combining shape information of the dental drill(s) that created the bore, shape information such as a CAD model of the drill(s). Thereby scan artefacts of the post and core model can be identified and/or removed. E.g. a notch or cut in the post and core model can be identified as a scan artefact by knowing that use of the particular drill used could not have provided such a notch or cut.

When a post and core, or a dental restoration comprising the post and core, is mounted in the mouth of a patient the insertion direction is not necessarily coinciding with the direction of the main axis of the post. Especially the adjacent teeth necessitate that care must be taken when designing the post and core model. The direction and structure of the tooth bore is often mainly determined by the root canal. Thus, in a further embodiment of the invention the insertion direction of the post and core is determined. This can e.g. be provided by taking into account the direction of the bore, the main axis of the bore, position and inclination of the lost tooth/teeth and adjacent teeth, structure of root canal, position and inclination of coping, and/or crown, position in the jaw and/or the like.

When processing the tooth during drilling or root canal therapy, the resulting bore may be highly irregular, in some cases because removal of the entire tooth root results in an irregular shape. Thus, in some cases a post and core model with a post exactly mirroring the bore is impossible to insert in the bore, e.g. due to undercuts in the bore. Another issue is when a determined insertion direction makes it impossible to insert the post and core into the bore. Therefore a further embodiment of the invention relates to performing undercut removal of the post and core model to allow for insertion of the post and core into the bore.

In a further embodiment of the invention the post and core model can be reduced, reshaped, optimised and/or changed to allow for a cement space or cement gap, such as a cement layer, when attaching or fixing the post and core in the bore. This can be provided manually, automatically and/or semi-automatically. E.g. a layer of certain predefined thickness which can be accounted for, e.g. by reducing the post and core model. The cement space may also have varying thickness depending on the structure of the bore. When accounting for the cement space, issues relating to the insertion direction and undercut removal may be relevant. E.g. the cement space is depending on the undercut area(s). The total volume of the cement space may also be calculated, possibly based on undercut removal, insertion direction, drill shape, scan artefacts, bore structure and the like. The total volume of the cement space may provide an indication of the necessary amount of binding material, such as cement, to use when mounting the final post and core in the bore.

A post and core typically comprises at least one rigid post to increase the strength. A rigid post such as a metal pin or metal post. Thus, a post and core may be custom designed around a standard (rigid) post. The rigid post may be present in the impression of the bore. I.e. the impression is provided with one or more rigid posts surrounded by impression material. The rigid post(s) in the impression may be the real post(s) used in the final post and core or may be a duplicate model of a rigid post. When scanning the impression the rigid post will become a part of the post and core model and/or the post model. Thus a post model may comprise a rigid post. In a further embodiment of the invention the post and core model is improved and/or optimised by integrating and/or merging shape information of the rigid post with the post and core model and/or the bore model and/or post model. Shape information in terms of e.g. a CAD model of the rigid post.

In a further embodiment of the invention the rigid post (i.e. the model of the rigid post) is identified, separated, removed, deleted and/or extinguished from the post and core model and/or the post model. This can be provided when having shape information of the post, i.e. the post can be "recognised" in the 3D post and core model. When knowing the shape of the post and when the post is identified in the 3D model, the post can also be taken out of the post and core model and/or the post model. Possibly leaving a hole/cavity/void in the post and core model and/the post model. Thereby a post and core model without post can be provided. Thereby the final post and core can be manufactured without the post, and the post may subsequently be inserted in the final post and core.

When taking the impression of the tooth and bore the dentist may use a longer post than the depth of the bore to facilitate control of the impression process, e.g. the post can be provided with a handle. After obtaining an impression scan this handle can be part of the post and core model. In a further embodiment of the invention the post is cut in the post and core model, preferably cut in a length relating to e.g. the dental restoration, the gingiva and/or the margin line.

In some embodiments the post and core margin line(s) are configured to be automatically arranged based on a margin area.

Thus the margin line for the post and core can be determined automatically or manually at the position where the post and core ends, e.g. in the end of the post and core, when arranged in the positive model.

In some embodiments the shape of the core and/or the coping and/or the crown are configured to be selected from a number of different predefined shapes.

An advantage of this embodiment is that the dental technician or user can select e.g. a core with the shape he wishes, or with a shape which suits the specific case. Hereby account can be taken of material requirements, thickness of the different layers of the restoration, etc. Using an anatomical reduction, the shape of the post and core can also be derived from the crown or coping shapes if these are designed prior to the post and core.

In some embodiments the shape of the core and/or the coping and/or the crown are configured to be changed by a digital sculpt-tool.

An advantage of this embodiment is that the dental technician can use the sculpt-tool to obtain design flexibility. The sculpt-tool may provide both a freeform and an automatic tool, e.g. a virtual wax knife, freeform morphing of any part of a surface, transformations for global repositioning, automatic smoothing, automatic minimum material enforcement and automatic high aesthetic cut to antagonist or gingival.

Some teeth may provide multiple root structure with multiple "main axes", i.e. root canals in multiple non-parallel directions. This is especially the case with the molar and premolar teeth. Thus, in a further embodiment of the invention the post and core is a split core, such as a split core for a multiple root tooth. This may provide a more advanced post and core model, e.g. comprising multiple non-parallel posts to strengthen the post and core.

Instead of inserting multiple posts in the bore of a multiple root structure a single post may provide enough strength for the post and core. The post and core is then designed around the single post, however the multiple root structure may need multiple post and core structure to fill the entire cavity of the multiple roots. In a further embodiment of the invention the bore is at least partly filled prior to inserting the post and core, preferably to simplify the necessary shape and structure of the post and core. This may for example be provided prior to obtaining an impression of the bore. Alternatively filling may be provided after obtaining an impression of the bore.

In some embodiments the method further comprises virtual filling of one of the bores when designing the post and core for a case with multiple bores, and then designing the post for the remaining bore(s).

In a further embodiment of the invention the post and core model and/or the dental restoration model is combined with or supplied with other imaging techniques, such as X-ray scans, CT scans, intraoral scans etc. X-ray image(s) of the prepared tooth and/or adjacent teeth may provide additional information of the bore and the prepared tooth, i.e. structure, volume, directions and/or the like. This can for example assist in identifying scan artefacts. X-ray imaging may also provide information of the general condition of the tooth, i.e. any hidden fractures of thickness of remaining bone structure. Typical features that are not obtained from the impression. Knowing the general condition of the tooth may also provide information of how much pressure can be applied to the prepared tooth and/or adjacent teeth, thereby for example being able to determine the length, shape, structure and/or thickness of the post to be applied and/or whether tooth enforcement, such as a tooth band, is necessary.

When designing the post and core model a correct fit to the bore is crucial. Thus, in a further embodiment of the invention, the bore model and the matching post and core model and/or post model can be visualised, preferably visualised concurrently. Preferably the match between the post and core model and/or the post model and the bore model can be visualised, such as visualised like plug-and-socket.

In some embodiments the method further comprises any of the steps of:
    providing an interface between the post and core model and the dental restoration model
    inverting the three dimensional impression model and/or merging the post and core model with a dental model comprising the prepared tooth, thereby obtaining a dental model comprising the prepared tooth and the bore,
    adding a base for the dental restoration model,
    determining the insertion direction of the dental restoration,
    removing scan artefacts, and/or
    adding at least one coping or crown to the model.

In another embodiment of the invention designing and/or manufacturing at least a part of a dental restoration comprising a post and core is provided. A post and core is typically part of a dental restoration. Thus, further steps are preferably provided to design the dental restoration around or on top of the post and core. The post and core model is provided by means of the positive model of the bore. However, the impression comprising the bore typically comprises a negative representation of the prepared tooth and the adjacent teeth. A positive dental model of these can e.g. be provided by inverting the three dimensional impression representation. A dental model can also be provided by scanning a cast model of the teeth and subsequently merging and/or combining the post and core model with the dental model. However, preferably both the post and core model and the dental model are provided from an impression scan. And preferably they are combined and visualised in a double sided rotatable 3D model as shown in FIGS. 3A and 3B, showing both the negative representation and positive model of post and core and teeth. Thus the virtual positive working model can be created from the scan representation of the impression.

A base may further be added to the dental restoration model. Preferably the insertion direction of the dental restoration is determined automatically or semi-automatically but may preferably also be adjusted manually by a user. In a further embodiment of the invention the dental restoration is a bridge.

In some embodiments the at least one coping or crown is automatically positioned on the post and core.

In some embodiments the position of the coping or crown is configured to be adjusted.

In some embodiments the crown and/or coping is designed before designing the post and core.

Thus either the crown and/or coping is designed first, and then the post and core is designed after this, such that the crown and/or coping determines the shape of the post and core, in particular determines the shape of the core, which the crown and/or coping is attached to.

Otherwise the post and core is designed first, and then the crown and coping is designed after this, such that the post and core determines the shape of the crown and/or coping.

In some embodiments the shape of the post and core is configured to be derived from the shape of the crown and/or the coping.

After root canal therapy a tooth may be severely reduced in strength. And mounting a post and core in the tooth vertical forces applied to the post and core (e.g. by chewing or jaw clenching) may be transferred to horizontal forces in the tooth root possibly leading to fracture in the root. This can be prevented by means of a tooth band applied around the tooth near the margin line and/or gingiva. This can be accounted for by applying, designing, integrating or merging a tooth band or a model of a tooth band to the dental restoration model. A tooth may be applied to the prepared tooth prior to the impression, and the tooth band or a negative representation of it, will therefore appear in the three dimensional model obtained from the impression. Preferably the dental model can be improved by combining and/or merging with shape information of tooth band, e.g. CAD models of tooth bands.

In some embodiments the post and core design automatically is retrieved from an electronic library, so that the post and core has a correct anatomical fit relative to the bore.

In some embodiments a cement gap in the bore is defined so that there is space for adding cement or glue into the physical bore before the post and core is fixed.

In a further embodiment of the invention combining, integrating and/or merging of impression scans obtained from multiple and/or different impressions are provided. This can for example be provided to improve the post and core model and/or the dental restoration model and/or the dental model. E.g. selected parts of a model can be rescanned, possibly in greater detail, and then merged into the original model. Single sided and/or double sided impressions and/or lower jaw dental impression and/or upper jaw dental impressions may be scanned, provided, and/or combined.

In some embodiments at least one of the steps are provided by means of CAD/CAM.

The present invention relates to different aspects including the method described above and in the following, and corresponding methods, devices, system and/or product means, each yielding one or more of the benefits and advantages described in connection with the first mentioned aspect, and each having one or more embodiments corresponding to the embodiments described in connection with the first mentioned aspect and/or disclosed in the appended claims.

In particular, the invention furthermore relates to a system comprising means for providing any of the listed methods. The invention furthermore relates to a computer program product comprising a computer readable medium, said computer program product comprising means for carrying out all the steps the listed methods.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein:

FIG. 1 shows a picture of a dental impression.

FIG. 11 shows an example of undercut areas in a preparation.

DETAILED DESCRIPTION

In the following description, reference is made to the accompanying figures, which show by way of illustration how the invention may be practiced.

FIG. 1a) is a picture of a dental impression comprising a standard rigid post for a post and core. The rigid post is shown in greater detail in the blow up.

FIG. 1b) is a picture of another dental impression comprising an impression of a bore. The impression of the bore is here made in a different material than the rest of the impression. The impression of the bore is irregular.

Figure 2:
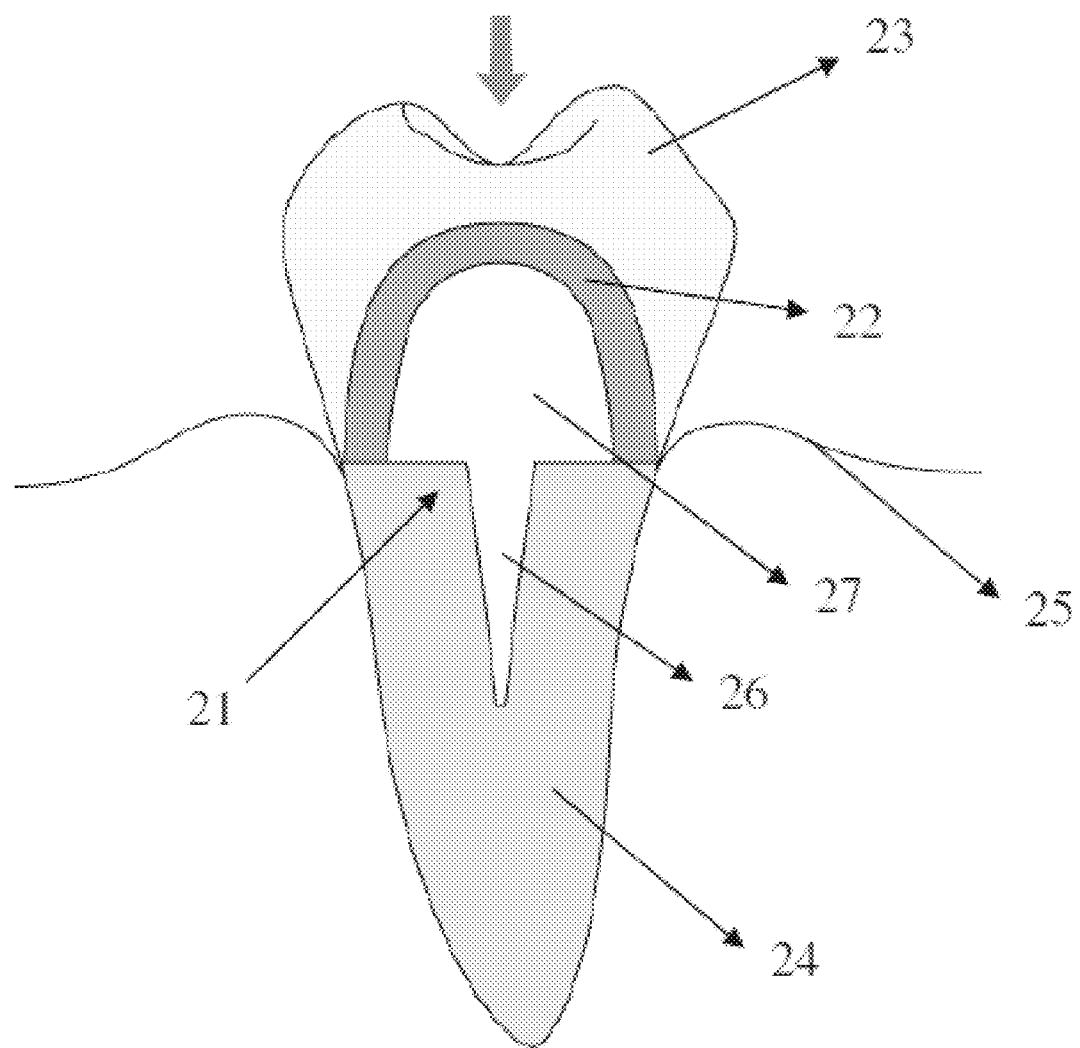
FIG. 2 schematically illustrates a dental restoration comprising a post and core.

FIG. 2 illustrates schematically a dental restoration comprising a post and core 21. The post and core 21 comprises the post 26 entering and matching the bore of the tooth 24 and the core 27 that provided retention of the coping 22 and the crown 23. The damaged tooth 24 has been prepared, i.e. it has been grinded down close to the gingiva 25 and a bore has been provided by means of a dental drill. The post and core 21 matches the bore of the prepared tooth 24. The post and core 21 also provides retention/support for the coping 22 and the crown 23. The post and core 21, the coping 22 and the crown 23 can all be designed/provided according to the present invention.

Figure 3A:
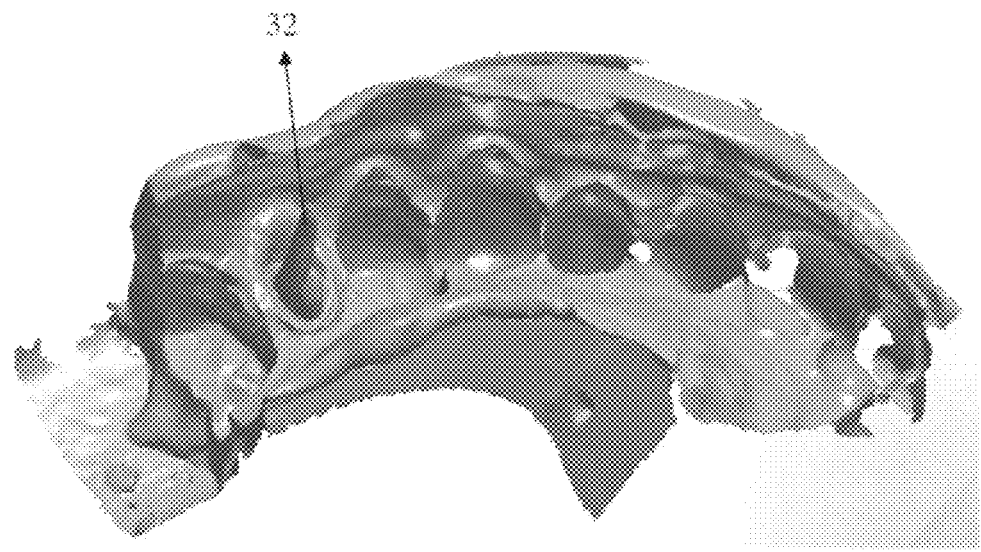
FIG. 3 shows a 3D model which is the result of an impression scan.
Figure 3B:
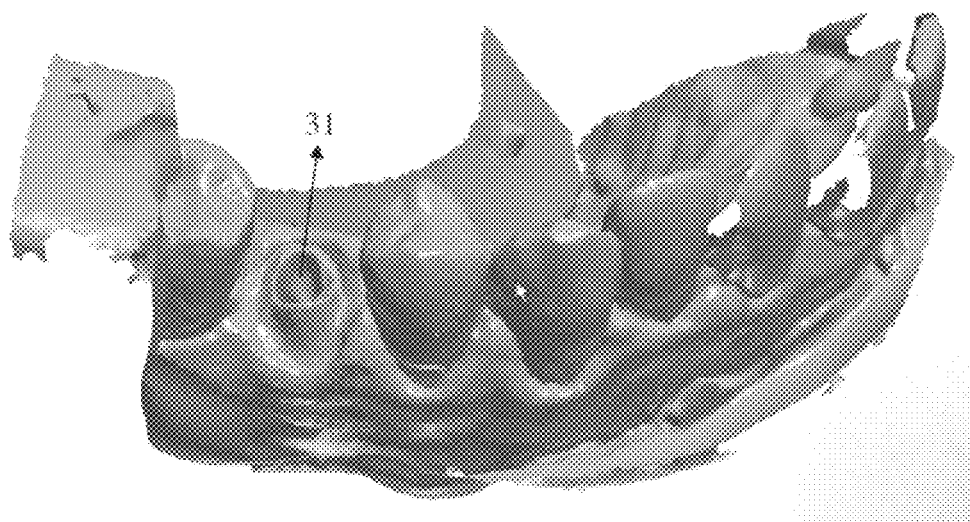
Figure 6:
FIG. 6 is a blow up of the post model in FIG. 3.

FIGS. 3A and 3B show a three dimensional model which is the result of an impression scan. FIG. 3A is the 3D scan representation of the impression showing the teeth in negative representation and with an impression 32 of the bore 31 forming a spike-like form becoming the basis for the post and core model. A blow up of the positive impression 32 is shown in FIG. 6.

FIG. 3B shows a virtual 3D positive model, e.g. working model, of the set of teeth and tooth bore, which is an inversion or transformation of the 3D representation of the impression in FIG. 3A. A dental restoration comprising a post and core can be designed according to the invention with basis in a 3D model as shown in FIG. 3.

Figure 4:
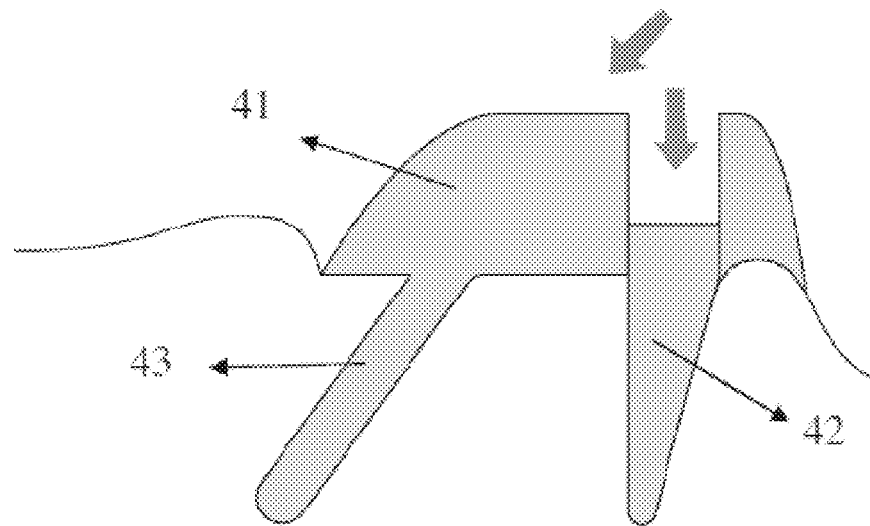
FIG. 4 schematically illustrates a post and core with two pins.

FIG. 4 illustrates a post and core with two posts 42, 43 and a core 41, for a tooth with multiple bores. Due to the different directions of the bores the post and core must be divided in at least two parts to provide insertion of both posts 42, 43 into the bores. In one embodiment of the invention design and/or manufacture of a post and core for a multiple bore tooth is provided. The post and core model is divided in at least two parts, such as a part for each bore, providing insertion of the post and core into the bore. Insertion directions for each part and/or for each bore are preferably provided.

Figure 5:
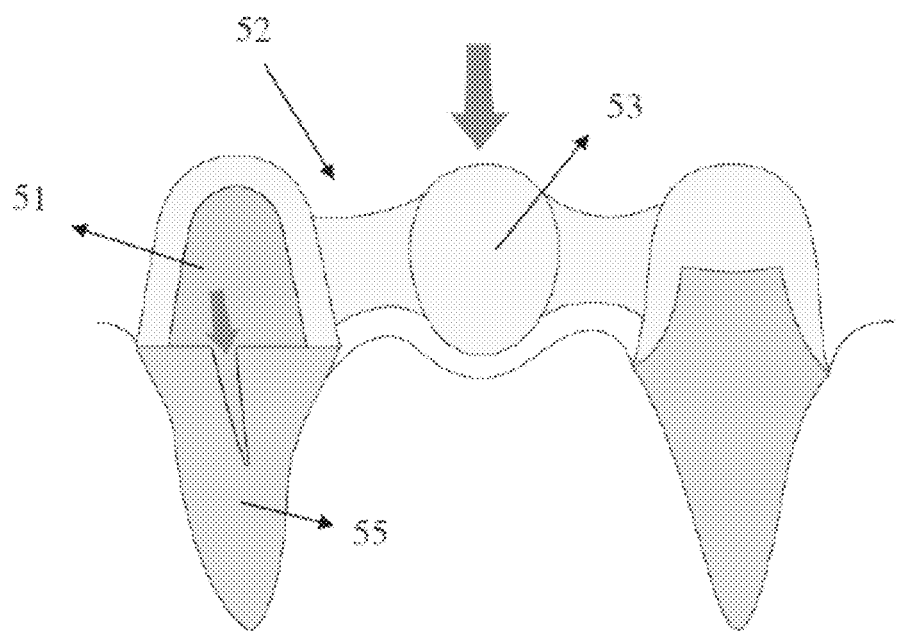
FIG. 5 schematically illustrates a dental bridge comprising a post and core.

FIG. 5 shows a model of a dental bridge 52 with retention in a post and core 51. The bridge 52 is provided to support the pontic 53 replacing a lost tooth. The post and core 51 provides retention for the bridge. With the thick arrows it is illustrated that the insertion directions of the post and core 51 and the bridge 52 are different. The post and core 51 is designed to match the bore 55 and the insertion direction of the post and core 51 is calculated to provide insertion of the post and core into the bore 55. However, the upper part of the post and core 51 providing retention for the bridge 52 is designed to be parallel with the calculated insertion direction of the bridge 52.

Figure 7:
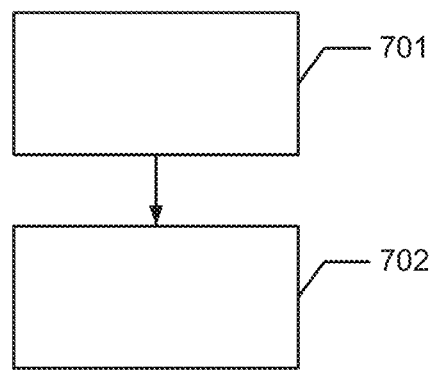
FIG. 7 is an example of a flow-chart showing the method.

FIG. 7 shows an example of a flow-chart of a method for designing and/or manufacturing a post and core to match a bore of a tooth. In step 701 scanning of at least one impression of the bore is performed. Preferably the impression is a dental impression comprising an impression of the bore, whereby a three dimensional model of the impression is obtained, where the three dimensional model comprises a positive model of the bore. In step 702 creation of a post and core model from the positive model of the bore is performed.

Figure 8:
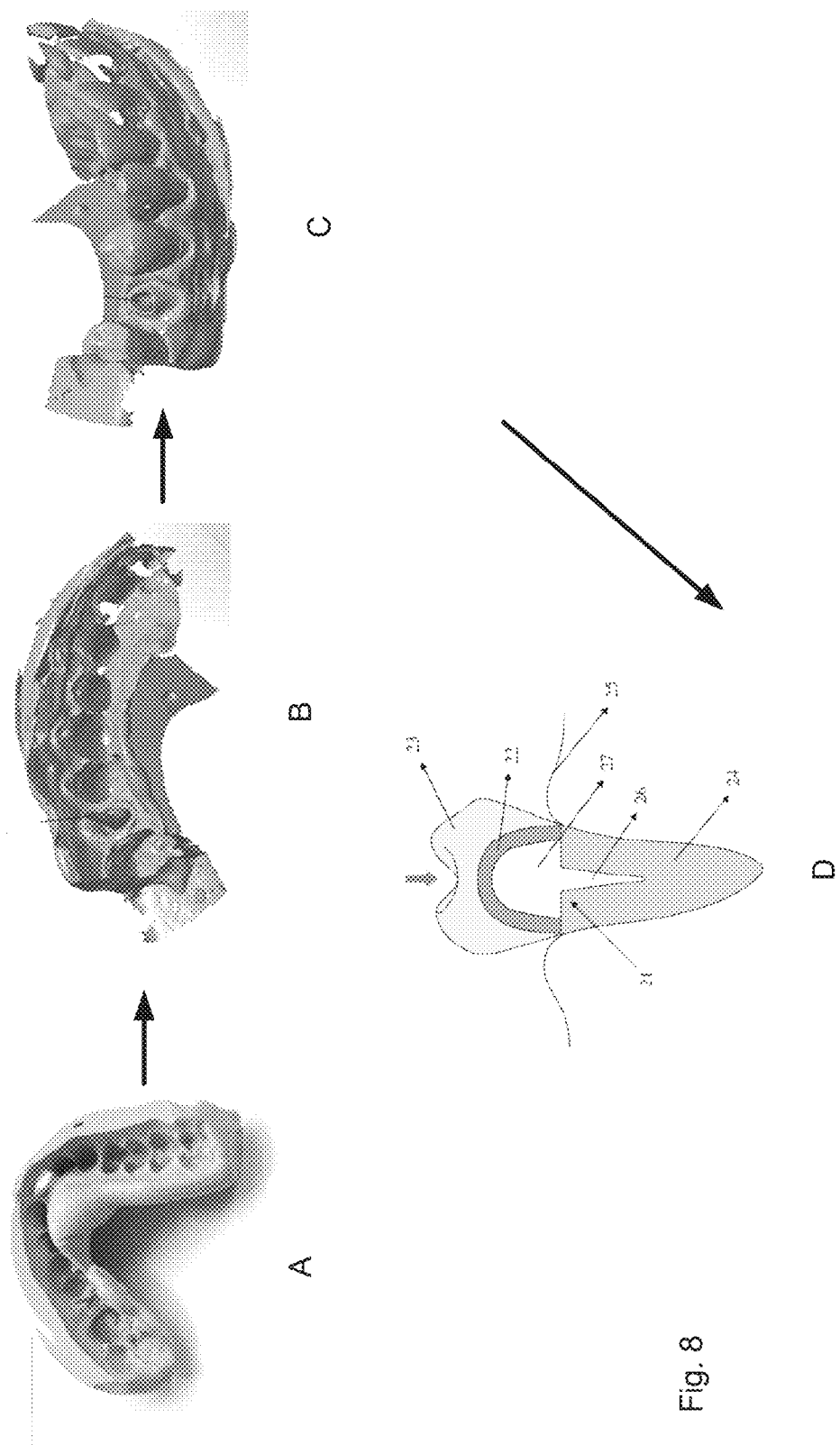
FIG. 8 shows the entire work flow of the method.

FIG. 8 shows an example of how the entire work flow can be according to the method.

In step A an impression is shown. The impression is made in a patient having a bore, into where a post and core should be fixed. A metal working-post is provided in the impression where the bore is, so in this case the bore forms a spike in the impression by means of the working-post. In other examples the bore forms a spike in the impression, where the spike is of the same material as the rest of the impression.

In step B the impression has been scanned, and the scanned image of the impression is shown. The bore is seen as a spike.

In step C a virtual positive model of the teeth is created from the scanned representation of the impression. The bore becomes a cavity in the positive model. Since both the negative representation and the positive model are available as digital images, the bore can be seen from all sides and there are no uncovered areas, whereby the post and core for fitting into the bore can be designed to fit perfectly into the bore.

In step D a drawing of a created post and core for perfect fitting into the bore is shown. The reference numbers on the drawing are explained in FIG. 2.

Figure 9:
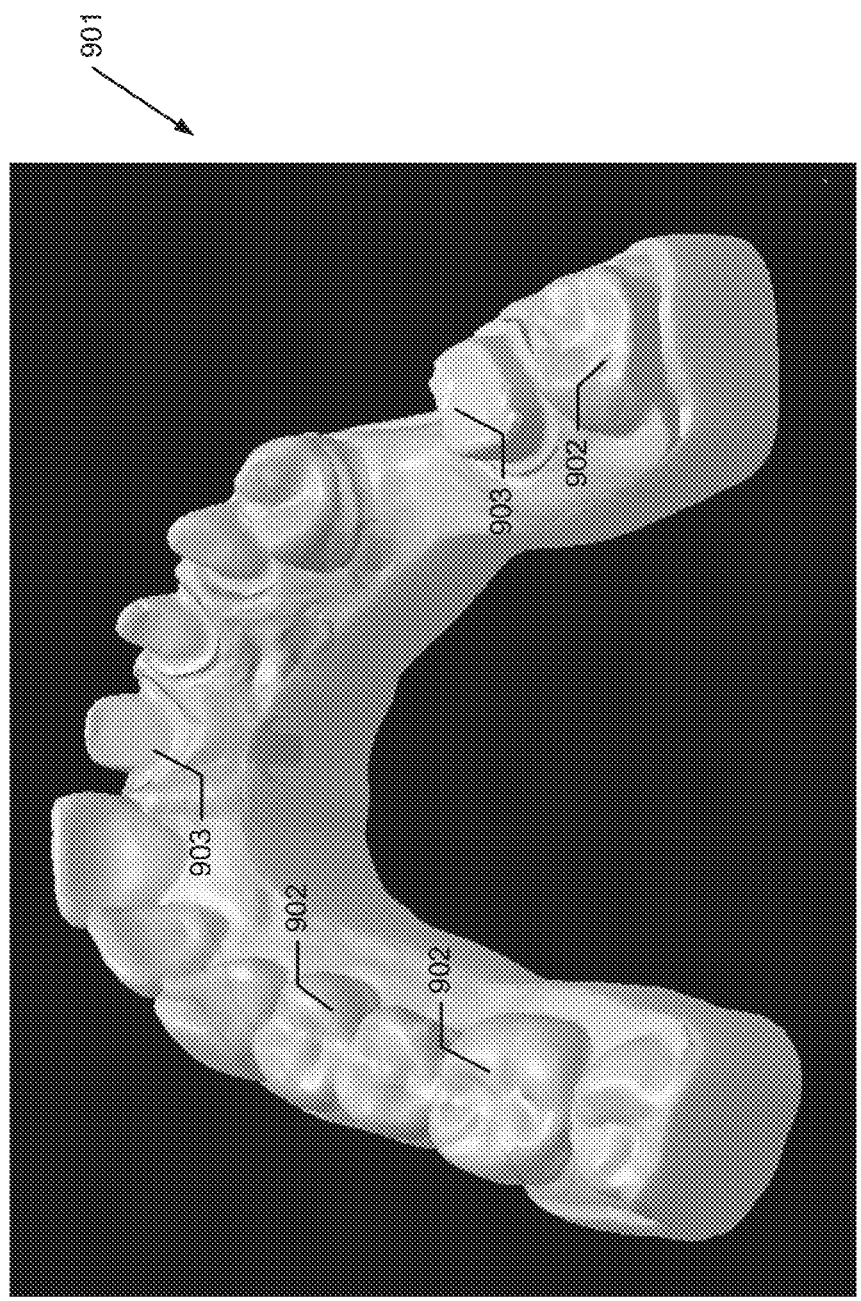
FIG. 9 shows an example of a virtual working model.

FIG. 9 shows an example of a virtual working model.

The virtual working model 901 comprises non-modified teeth 902 and prepared teeth 903, which are prepared for dental restorations. One of the prepared teeth 903 or dental restorations may be a post and core restoration. The working model in the figure has been trimmed, i.e. the scans forming the model are trimmed, the model is provided with a base and with sectioned preparations preserving the gingival. Furthermore, the model can be articulation tested.

FIG. 10 shows examples of different steps which can be used when designing a post and core.

FIG. 10a) shows the post and core model 101, where the dots 102 indicate the area of the margin line 103.

FIG. 10b) shows the post and core model 101 with an indication of the insertion direction 104 of the bore or post 105.

Figure 10C:
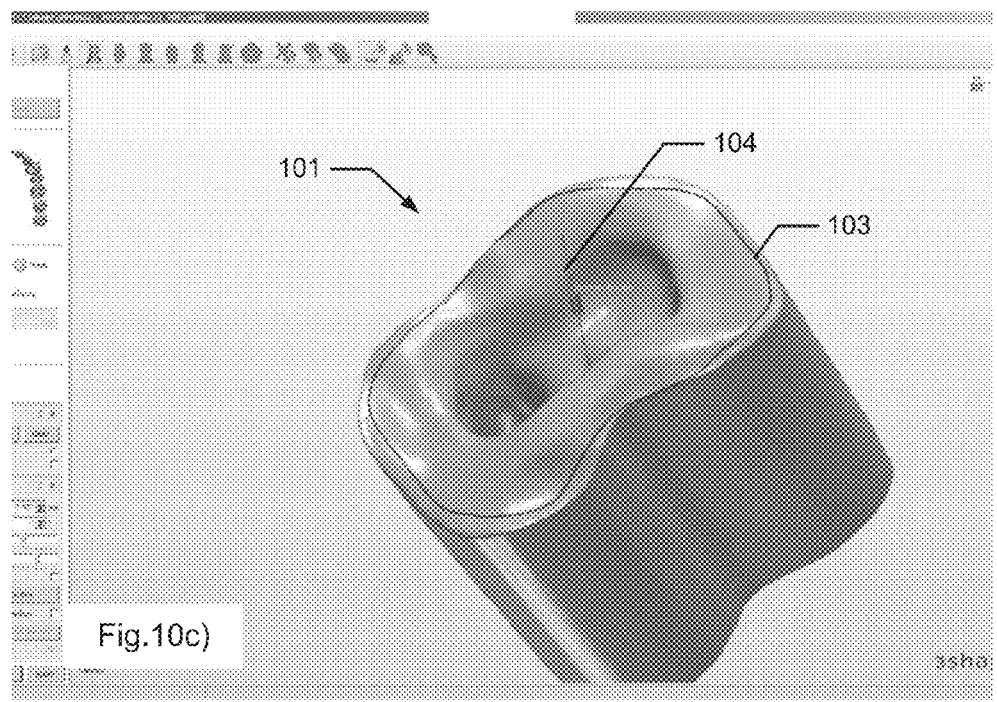
FIG. 10 shows examples of different steps which can be used when designing a post and core.

FIG. 10c) shows the post and core model 101 with insertions direction 104 and margin line 103.

Figure 10D:
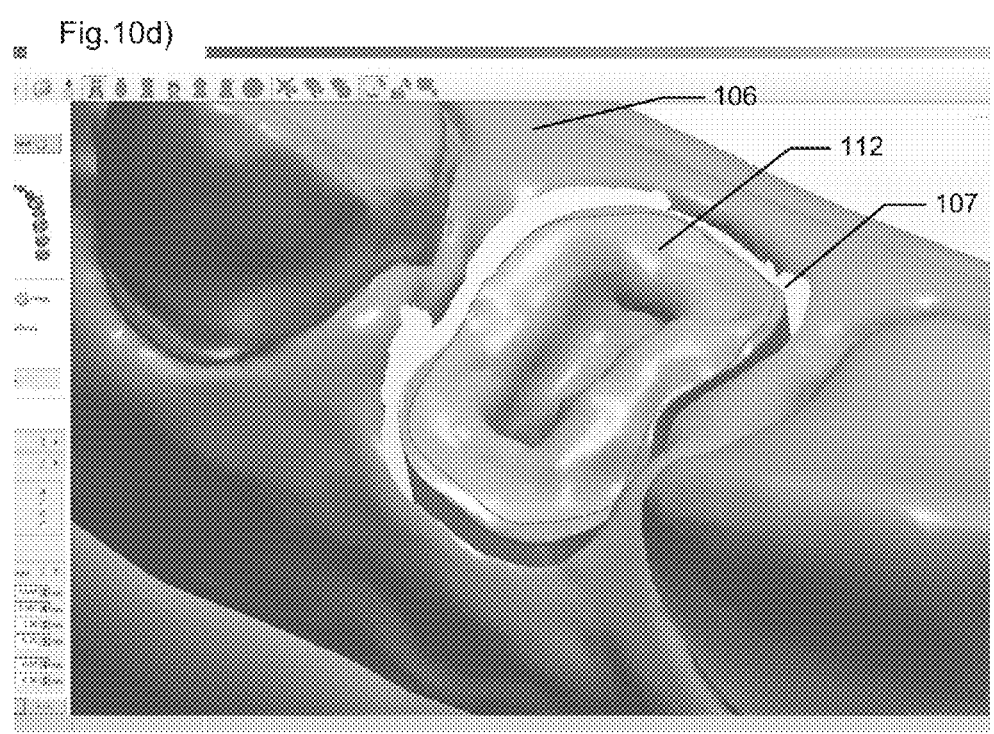

FIG. 10d) shows the designed post and core model 112 fitted into the full model 106, or working model or model of the rest of the set of teeth, or dental model. A cement space 107 is included between the designed post and core model 112 and the model 106.

FIG. 10e) shows a cross-section 108 through the model 106 and through the post and core model 112. The image in lower right part of FIG. 10e) shows this cross-section, where the cement space 107 is also seen.

FIG. 10f shows the model 106 and a crown 109 attached to the designed post and core.

Figure 10G:
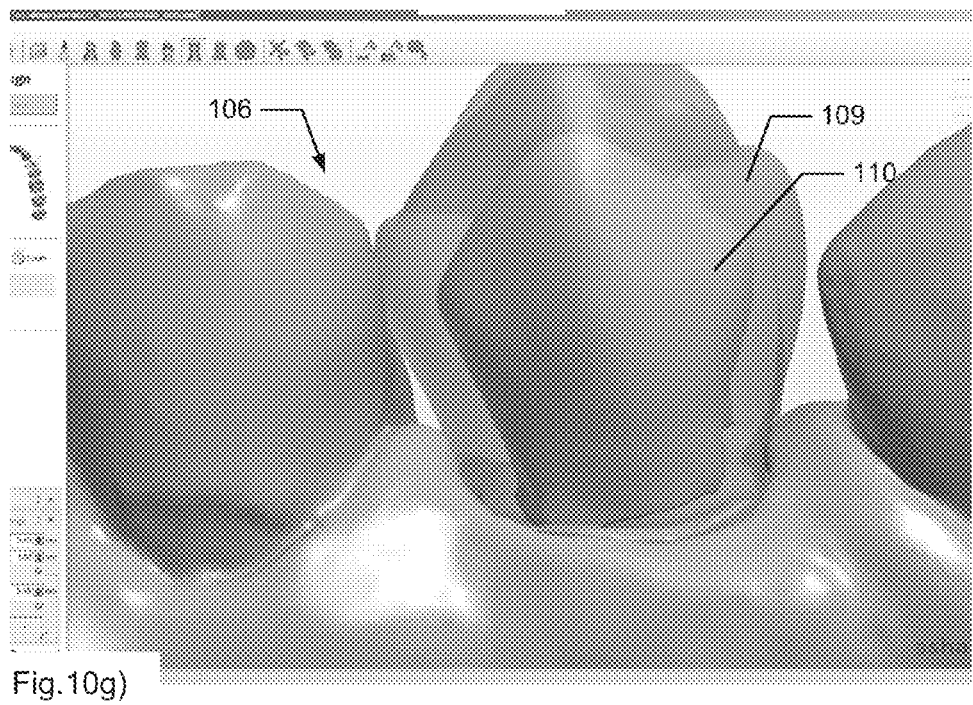

FIG. 10g) shows the model 106 and the crown 109 and the core 110 underneath the crown, where the crown 109 has been adjusted to fit the model 106.

Figure 10H:
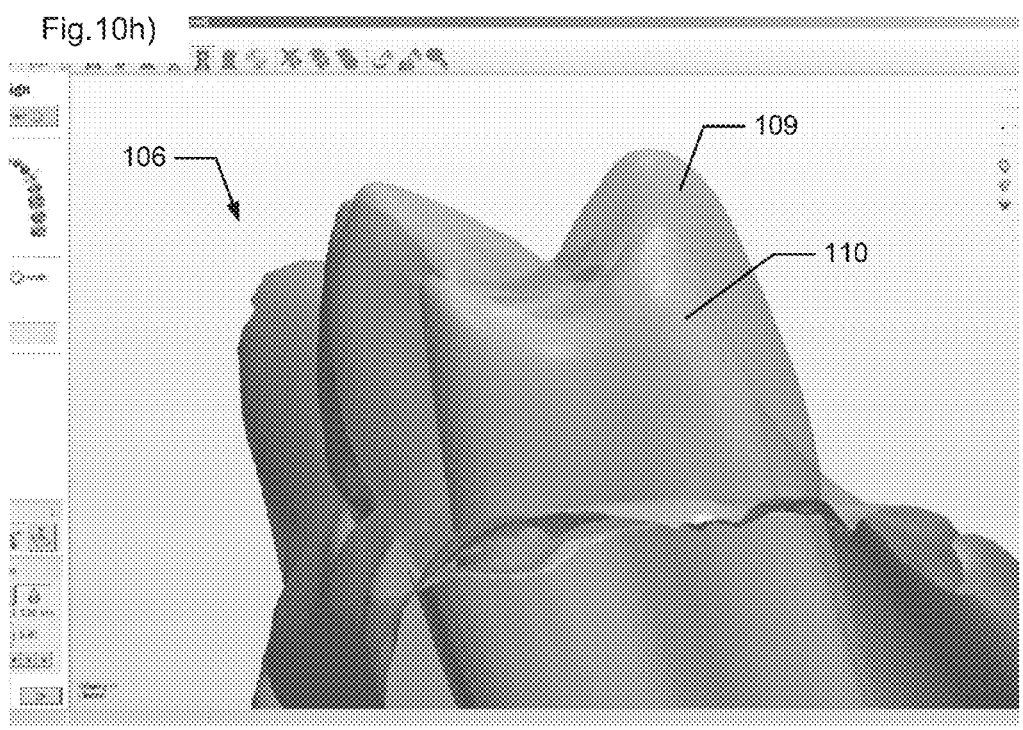

FIG. 10h) shows the model 106 and the crown 109 and the core 110, where undercut removal of the core 110 has been performed, such that the attachment of the crown 109 to the core 110 will be unproblematic.

FIG. 10i) shows the complete post and core 112 in the model 106, where the post and core comprises the core 110 and the post 111.

FIG. 11 shows an example of undercut areas in a preparation.

The figure shows why a scanner cannot obtain image information of undercuts or hidden areas in a preparation. A scanner 201 comprises a light projection 202 and a camera 203 for capturing the reflected light. The scanner 201 is scanning a tooth preparation 204 with undercuts 205, but as seen the scanner cannot obtain image information at the undercuts 205, because the light projection 202 and/or the camera 203 cannot gain access to the points of the undercut. Thus the undercuts are uncovered areas.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hard-wired circuitry instead of software or in combination with software.

The invention claimed is:

1. A computer-implemented method of designing and/or manufacturing a post and core to match a bore of a tooth, said method comprising the steps of:
   a) obtaining at least one negative impression of a set of teeth comprising a bore such that the negative impression includes a positive projection representing the bore;

b) scanning the negative impression of the set of teeth comprising the bore;

c) providing a three-dimensional scan representation of the negative impression comprising the positive projection representing the bore;

d) transforming the three-dimensional scan representation to a three-dimensional positive working model of the set of teeth and the bore; and e) designing a post and core model from the positive working model of the bore, wherein a post of the post and core matches the bore of the tooth such that a distance from an outer surface of the post to the closest portion of the bore of the tooth is substantially the same throughout the post.

2. The method according to claim 1, wherein the virtual three-dimensional working model is configured to be trimmed, and/or provided with a base, and/or articulation tested, and/or provided with sectioned preparations preserving the gingival.

3. The method according to claim 1, wherein manufacturing comprises manufacturing the post and core design and/or manufacturing the working model.

4. The method according to claim 1, wherein the step of scanning the at least one negative impression comprises: a performing an initial scan of the impression; b creating a visibility function based on a virtual model of the scanner performing the scanning and the initial scan of the at least one negative impression, said visibility function being capable of evaluating the coverage of areas of interest of the at least one negative impression by at least one predetermined scan sequence; c establishing at least one scan sequence based on the evaluation of the visibility function; d performing a scan of the at least one negative impression using said at least one scan sequence; e optionally repeating steps c) and d) at least once until the three dimensional model of the at least one negative impression is obtained.

5. The method according to claim 1, further comprising the step of matching the post and core model with the shape of the dental drill that created the bore.

6. The method according to claim 1, further comprising the step of improving the post and core model and/or the bore model by combining with shape information of the dental drill that created the bore, shape information such as a CAD model of the drill.

7. The method according to claim 1, further comprising the step of determining the insertion direction of the post and core.

8. The method according to claim 1, further comprising the step of performing undercut removal of the post and core model to allow for insertion of the post and core into the bore along said insertion direction.

9. The method according to claim 1, further comprising the step of reshaping the post and core model to allow for a cement space, when fixing the post and core in the bore.

10. The method according to claim 1, wherein the post and core comprises at least one predefined and/or standard rigid post and/or wherein the impression of the bore comprises the rigid post or a model of the rigid post.

11. The method according to claim 1, further comprising the step of integrating shape information of the post with the post and core model and/or the bore model.

12. The method according to claim 1, wherein a post and core is manufactured without the post on the basis of the post and core model and wherein the post and core model comprises a predefined bore for the post.

13. The method according to claim 1, wherein the post and core is a split core, such as a split core for a multiple root tooth.

14. The method according to claim 1, further comprising virtual filling of one of the bores when designing the post and core for a case with multiple bores, and then designing the post for the remaining bore(s).

15. The method according to claim 1, further comprising the step of providing and/or using and/or combining with one or more different imaging techniques, such as X-ray imaging, CT scans, intraoral scans.

16. The method according to claim 1, for designing and/or manufacturing at least a part of a dental restoration comprising a post and core, said method further comprising any of the steps of:

providing an interface between the post and core model and the dental restoration model inverting the three dimensional impression model and/or merging the post and core model with a dental model comprising the prepared tooth, thereby obtaining a dental model comprising the prepared tooth and the bore, adding a base for the dental restoration model, determining the insertion direction of the dental restoration, removing scan artefacts, and/or adding at least one coping or crown to the model.

17. The method according to claim 1, wherein the at least one coping or crown is automatically positioned on the post and core.

18. The method according to claim 1, wherein a crown and/or coping is designed before designing the post and core.

19. The method according to claim 18, wherein the shape of the post and core is configured to be derived from the shape of the crown and/or the coping.

20. The method according to claim 1, wherein the post and core design automatically is retrieved from an electronic library, so that the post and core has a correct anatomical fit relative to the bore.

21. The method according to claim 1, further comprising the step of scanning at least a part of an upper jaw dental impression and/or a lower jaw dental impression, at least one impression comprising an impression of the bore.

22. A system for designing and/or manufacturing a post and core to match a bore of a tooth and/or for designing and/or manufacturing at least a part of a dental restoration comprising a post and core, said system comprising means for providing any of the steps of any of the methods according to claim 1.

23. A nontransitory computer program product having a computer readable medium, said computer program product providing a system for designing and/or manufacturing a post and core to match a bore of a tooth and/or for designing and/or manufacturing at least a part of a dental restoration comprising a post and core, said computer program product comprising means for carrying out all the steps of the methods according to claim 1.

* * * * *